(12) United States Patent
Sanders et al.

(10) Patent No.: US 9,839,418 B2
(45) Date of Patent: Dec. 12, 2017

(54) PASSIVE RETRIEVING INTEROSSEOUS SUTURE PASSING DEVICE

(71) Applicant: TENSOR SURGICAL, INC., Chattanooga, TN (US)

(72) Inventors: Brett Sanders, Signal Mountain, TN (US); Keith J. Harper, Chattanooga, TN (US)

(73) Assignee: TENSOR SURGICAL, INC., Chattanooga, TN (US)

( * ) Notice: Subject to any disclaimer, the term of this patent is extended or adjusted under 35 U.S.C. 154(b) by 132 days.

(21) Appl. No.: 14/911,764

(22) PCT Filed: Aug. 28, 2014

(86) PCT No.: PCT/US2014/053050
§ 371 (c)(1),
(2) Date: Feb. 12, 2016

(87) PCT Pub. No.: WO2015/031559
PCT Pub. Date: Mar. 5, 2015

(65) Prior Publication Data
US 2016/0183934 A1 Jun. 30, 2016

(51) Int. Cl.
*A61B 17/04* (2006.01)
*A61B 17/16* (2006.01)
*A61B 17/17* (2006.01)
*A61B 17/06* (2006.01)

(52) U.S. Cl.
CPC .......... *A61B 17/04* (2013.01); *A61B 17/0482* (2013.01); *A61B 17/0485* (2013.01); *A61B 17/06109* (2013.01); *A61B 17/1604* (2013.01); *A61B 17/1714* (2013.01); *A61B 17/1778* (2016.11); *A61B 17/1796* (2013.01); *A61B 2017/06042* (2013.01)

(58) Field of Classification Search
CPC  A61B 2017/00353; A61B 2017/00358; A61B 2017/00349; A61B 2017/00473; A61B 2017/0408; A61B 2017/0409; A61B 2017/0414; A61B 2017/0445; A61B 2017/06042; A61B 17/0401; A61B 17/0469; A61B 17/0482; A61B 17/0483; A61B 17/0485; A61B 17/17; A61B 17/1714; A61B 17/1717; A61B 17/1796
See application file for complete search history.

(56) References Cited

U.S. PATENT DOCUMENTS

| | | | | |
|---|---|---|---|---|
| 5,741,279 | A * | 4/1998 | Gordon | A61B 17/0469 216/56 |
| 7,722,630 | B1 * | 5/2010 | Stone | A61B 17/0491 606/144 |
| 2007/0203507 | A1 * | 8/2007 | McLaughlin | A61B 17/0057 606/144 |

(Continued)

*Primary Examiner* — Robert Lynch
(74) *Attorney, Agent, or Firm* — Carothers & Carothers

(57) ABSTRACT

A passive retrieving interosseous suture passing instrument (10) having a guide handle (13) with a proximal end for grasping and a distal end for engagement with a bone (11) to which suture (22) is to be attached. The bone (11) is provided with a first tunnel (15), and a suture retrieving arm (12) carried at the distal end of the guide handle (13) is provided with a distal tip dimensioned to be received in the first tunnel (15).

5 Claims, 10 Drawing Sheets

(56) References Cited

U.S. PATENT DOCUMENTS

2011/0009867 A1\* 1/2011 Oren .................. A61B 17/0482
                                                    606/80
2012/0303046 A1\* 11/2012 Stone ................. A61B 17/0469
                                                    606/145

\* cited by examiner

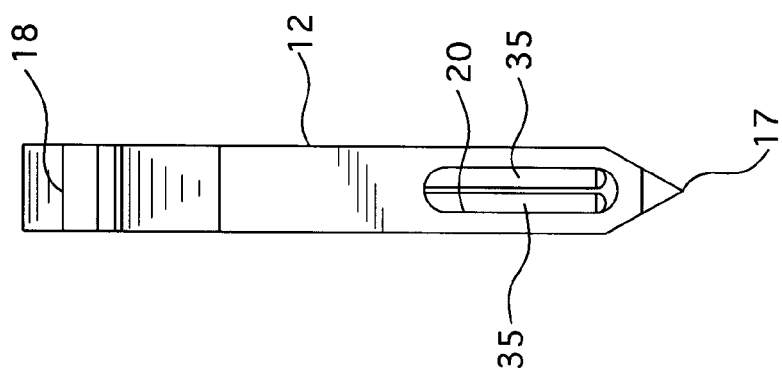
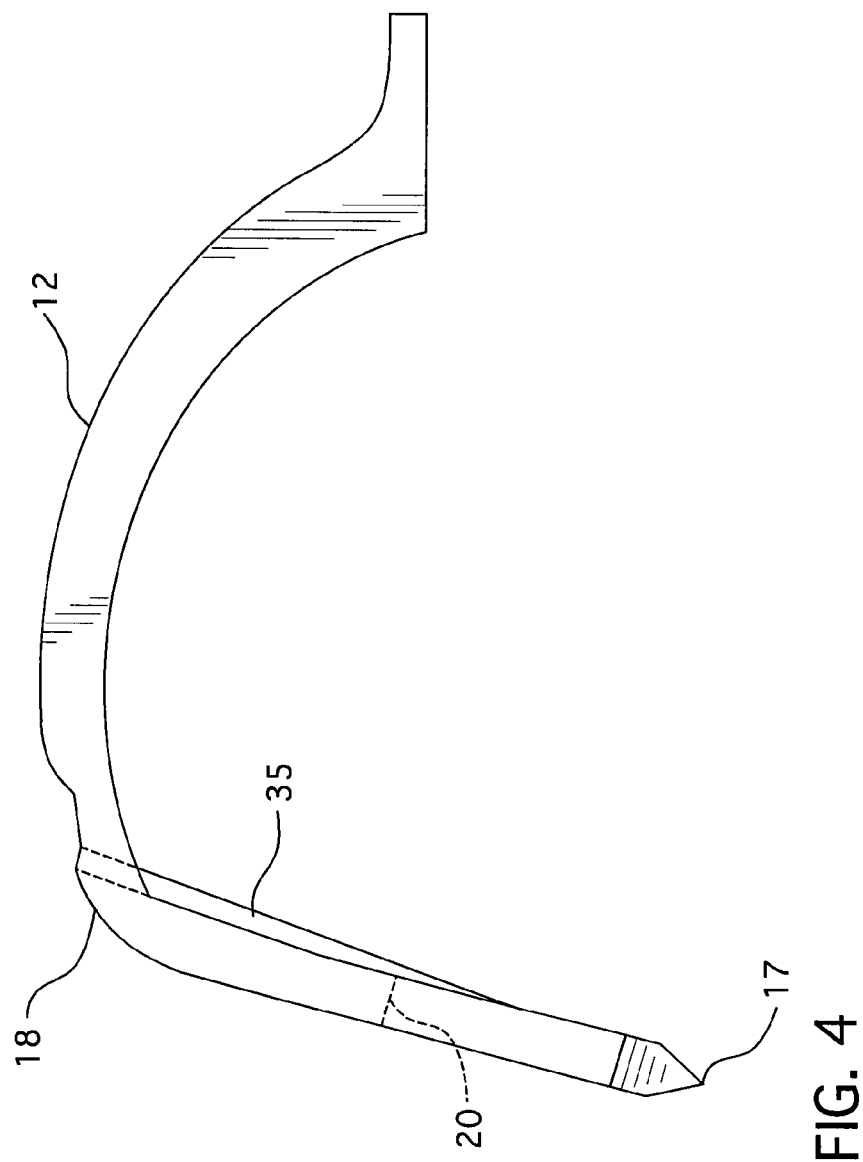
FIG. 5
FIG. 4

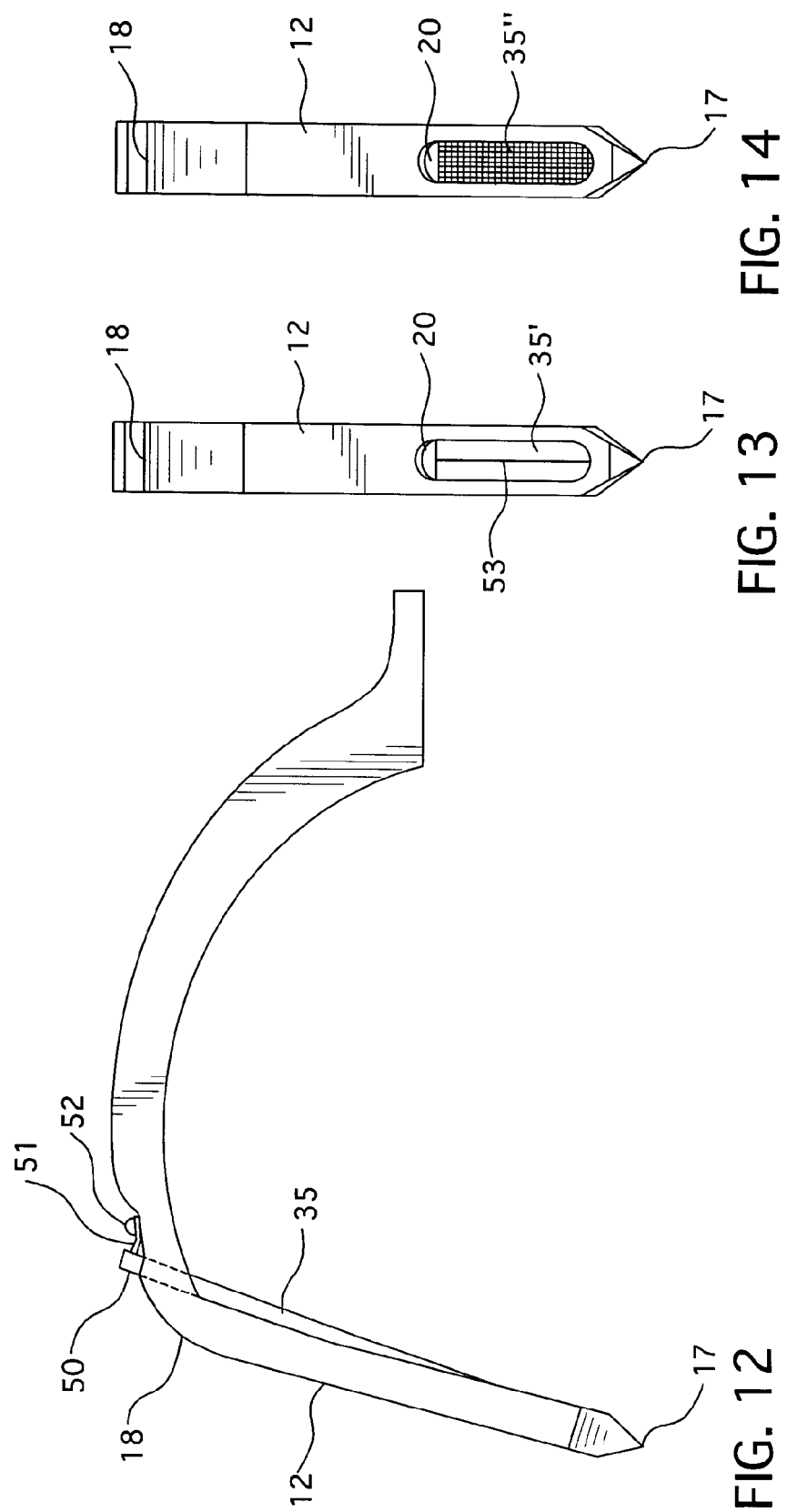

PASSIVE RETRIEVING INTEROSSEOUS SUTURE PASSING DEVICE

CROSS REFERENCE

This application claims the benefit of International Patent Application No. PCT/US2013/057485, filed on 30 Aug. 2013, for Transosseous Attachment Method and Instruments and U.S. Provisional Patent Application No. 62/025,044, filed on 16 Jul. 2014, for Passive Retrieving Interosseous Suture Passing Device, the entire contents of which are incorporated herein by reference.

BACKGROUND OF THE INVENTION

The invention relates to techniques and instruments for surgical transosseous attachments, for example, the attachment of ligaments, tendons, fascia, and muscle to an adjacent bone to effect a repair of a joint. Typical joints subjected to repair are the hands, feet, ankle, knee and shoulder.

Transosseous attachment instruments of the type presently described, are generally referred to as a tunneler as they are not only utilized for the transosseous passing of suture, but in addition, are generally utilized to also guide bone tunneling procedures. Tunneler instruments of the prior art are at a disadvantage in that they require excessive procedural step to form the intersecting tunnels and transosseously pass suture through the intersecting tunnels. In addition, the prior art tunneler instruments cannot assure quick and effective transosseous placement and passing of the suture on each and every attempt, and in addition, the prior tunneler instruments are generally single use instruments which cannot be readily disassembled, disinfected and reused.

Tunneler instruments of the prior art such as illustrated in U.S. Pat. No. 8,449,552, issued on May 28, 2013, for Surgical Drill Guide with Awl and Method of Use, do not provide a passive means for capturing the suture and therefore quick and effective transosseous placement, and passing of the suture cannot be assured on each and every attempt. With this and other prior art tunnelers, in order to capture the suture passed through a suture retrieving element, additional active manipulation of the suture retrieving element must be taken in order to effect capture of the suture to be retrieved, and assured capture of the suture upon active manipulation of the suture retrieving element cannot be guaranteed.

It is therefore an object of the present invention to provide an interosseous suture passing tunneling device which possesses passive retrieving capabilities in the suture retrieving element of the tunneler and which absolutely assures quick and effective transosseous placement and passing of the suture on each and every attempt.

SUMMARY OF THE INVENTION

The passive retrieving interosseous suture passing instrument of the present invention includes a guide handle having a proximal end for manual grasping and a distal end for engagement with a bone to which suture is to be attached, the bone being provided with a first tunnel. A suture retrieving arm is carried at the distal end of the guide handle and it is provided with a distal tip which is dimensioned to be received in this first bone tunnel. The retrieving arm is also provided with a window therethrough which is aligned with a central guide bore passing through the handle for receiving a bone tunneling implement, such as a drill or awl, to form a second intersecting tunnel in the bone which passes through the window.

A suture passing awl is provided which is dimensioned and configured to be received in the central guide bore of the guide handle and to carry and pass suture through the window for capture and retention in the window of the suture retrieving arm. The instrument of the present invention is characterized by a passive suture capture device in the window which is adapted to passively engage suture carried on the awl under a pinching spring biased engagement sufficient to prevent withdrawal of the suture from the window when the awl is withdrawn, thus always insuring effective transosseous placement and passing of the suture on each and every attempt.

The passive suture capture device may take on various forms. In one of the more preferred embodiments, the passive suture capture device is comprised of a spaced pair of nitinol wires having their free distal ends depending into the window and positioned for passage of the suture passing awl therebetween under spring biased engagement of the nitinol wires against the suture being carried on the awl. Preferably the nitinol wires are replaceable and the suture retrieving arm carrying the nitinol wires includes spring clips for retaining the proximal ends of the replaceable nitinol wires.

The awl is keyed to the guide handle for guided orientation relative to the handle when fully seated therein to ensure proper orientation of the suture carried on the awl for engagement with the passive suture capture device. The awl is also preferably pointed at its distal end for creating a bone tunnel while simultaneously carrying the suture, which is exposed on the sides of the awl.

In a different embodiment, the suture capture device may consist of a flexible and penetrable capture wall confined within the window of the suture retrieving arm, such as a wall or sleeve of silicone or a wall of one or more layers of a fine mesh, such as a metal or plastic mesh. Alternatively the suture capture choice may consist of a metal trap door configuration.

The suture retrieving arm of the instrument may be constructed of one piece or may be constructed of two pieces which are interconnected and include a detachable oriented bone tunneling spike at the forward distal end of the suture retrieving arm, and wherein the spike carries the suture passing window at its distal end.

BRIEF DESCRIPTION OF THE DRAWINGS

Other objects and advantages appear hereinafter in the following description and claims. The accompanying drawings show, for the purpose of exemplification, without limiting the scope of the present invention or the appended claims, certain practical embodiments of the present invention wherein:

FIG. 4 is an enlarged view in side elevation of the passive suture retrieving arm which is positioned on the forward end of the tunneler instruments shown in FIGS. 1, 2 and 3;

FIG. 5 is a front view of the passive suture retrieving arm shown in FIG. 4;

FIG. 12 is an enlarged view in side elevation of the passive suture retrieving arm illustrated in FIG. 4 with the addition of steel spring clips retaining the proximal ends of the replaceable nitinol wires utilized for the passive suture capturing device;

FIG. 13 is an enlarged front view of the passive suture retrieving arm incorporating another embodiment of the passive suture capture device in the retrieving arm window in the form of a metal trap door;

FIG. 14 is an enlarged front view of the passive suture retrieving arm illustrating another embodiment of the passive suture capture device in the suture passing window of the arm in the form of one or more layers of a fine metal or plastic mesh.

DETAILED DESCRIPTION OF PREFERRED EMBODIMENTS

The following illustrated examples depict instruments and techniques to pass a suture through a portion of the head of the humeral bone at the shoulder of a human patient to repair damaged soft tissue associated with the shoulder joint. However, instruments and techniques according to the present invention may be used to pass a suture through any joint bone.

Figure 11:
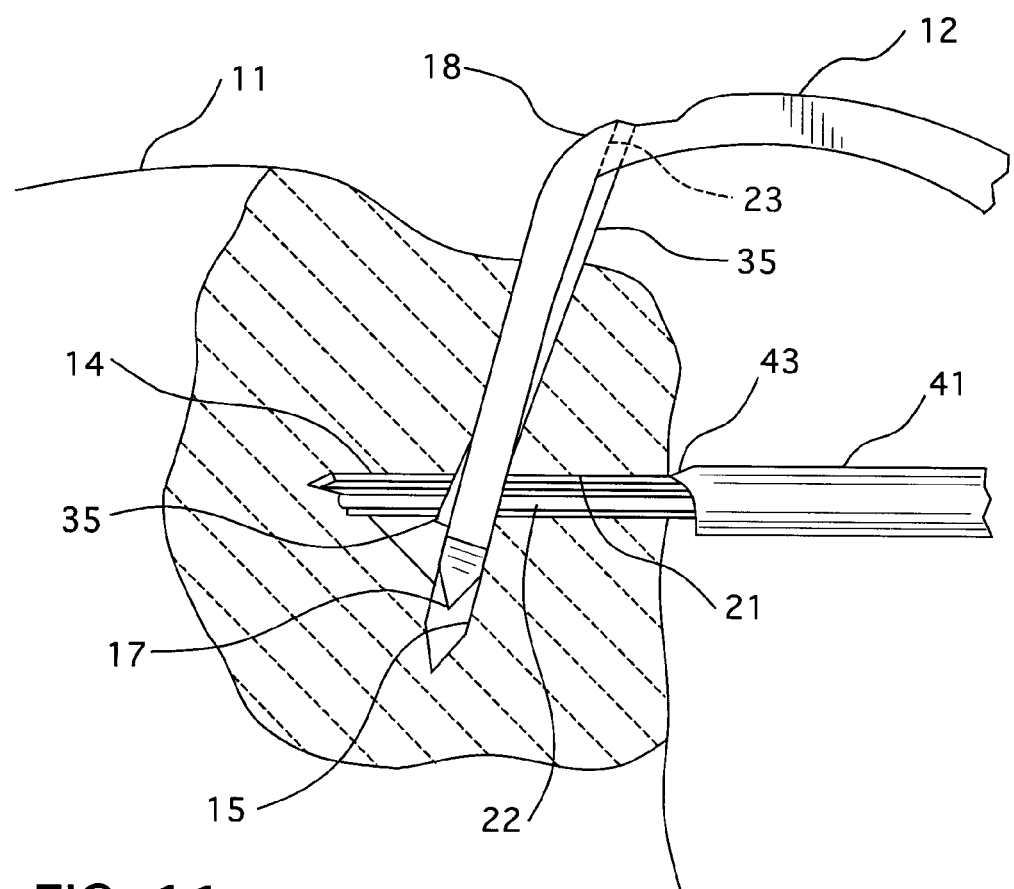
FIG. 11 is a side view in partial section illustrating the application of the tunneler instrument of the present invention to a humeral head.

Referring to the drawings, the tunneler instrument 10 is utilized for the creation of converging tunnels in bone (transosseous tunneling) both arthroscopically or with open techniques. For illustration purposes only, the tunneler 10 of the present invention is illustrated in the creation of tunnels in the humeral head 11 shown in FIG. 11 to allow for the repair of a torn rotator cuff.

The tunneler instrument 10 consists of a guide handle 13 having at its forward end a passive suture retrieving arm 12, and a suture pusher awl 14. These elements work together to assist in creating two converging tunnels of different length and angles within bone and transosseously pass suture through the tunnels utilizing a passive suture capture or retrieving device on the distal end of suture retrieving arm 12 which interacts with the forward distal end of suture passer awl 14. The tunneler instrument 10 transosseously passes and passively captures and retrieves suture 22 through the lateral tunnel 21 and medial tunnel 15 respectively, with fewer steps and greater reliability and repeatability than is possible through the use of current techniques.

Figure 9:
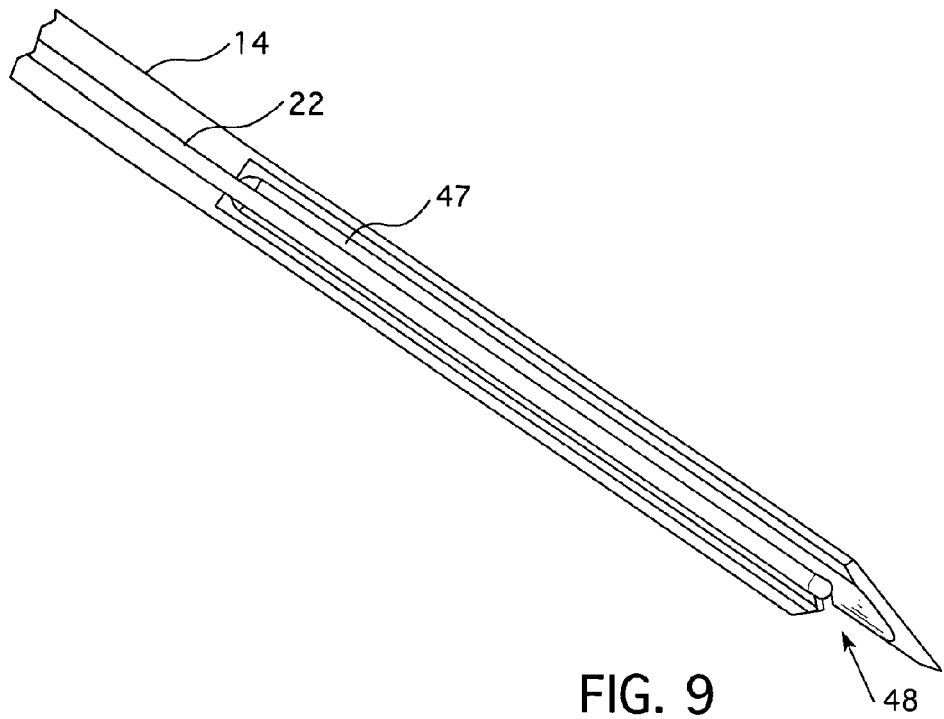
FIG. 9 is an enlarged perspective view of the forward end of the suture pushing awl loaded with a suture.

An awl or drill (not shown) is first used to create the first or medial tunnel 15 (FIG. 11) in the humeral head 11. The passive suture retriever arm 12 is constructed of surgical stainless steel or other suitable material and is provided with a sharp distal tip 17 for piercing tissue, such as the percutaneous penetration of the deltoid and to also penetrate the rotator cuff, if desired, thereby eliminating a step. Window 20 is provided in the distal end of arm 12 to allow passage of the complimentary pusher awl 14, which is used to create the second converging lateral tunnel 21, as well as for passing suture 22 through the lateral tunnel. With specific reference to FIGS. 9 and 10, suture pusher awl 14 has a special "shark mouth" geometry such that a slot 48 is created in the distal tip allowing it to retain a loop of the suture 22 in slot 48 and in side grooves 47 while creating the tunnel 21, but releases the suture 22 as it is withdrawn from the tunnel 21.

The head 18 of passive suture retrieving arm 12 is provided with two side by side passages 23 to receive and tightly retain the upper ends of nitinol wires 35 which have their free distal ends depending downwardly into open window 20 for passively capturing and retrieving suture 22 from the distal end of awl 14.

Figure 1:
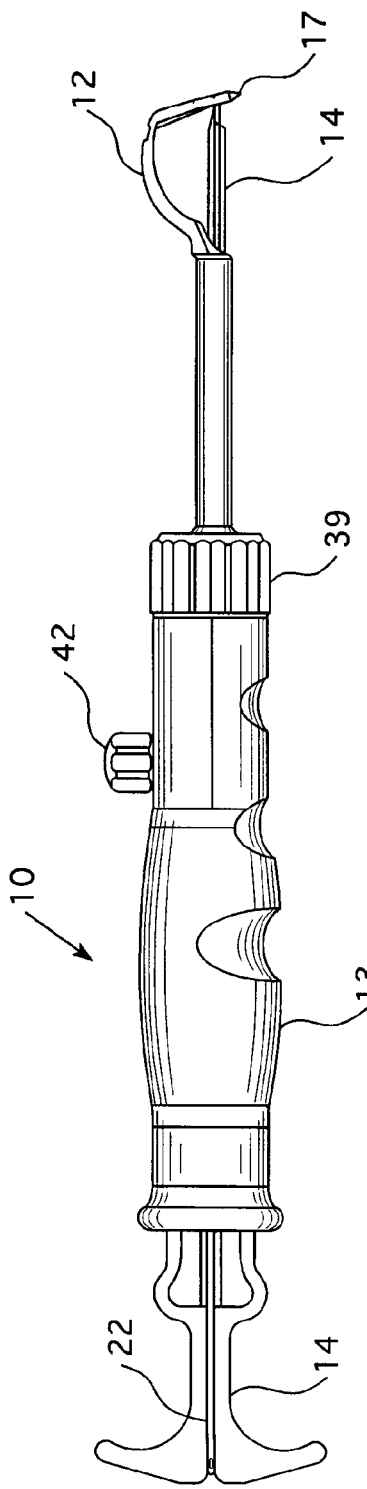
FIG. 1 is a side view of one embodiment of the tunneler instrument of the present invention showing the suture pushing awl partially inserted into the instrument.
Figure 2:
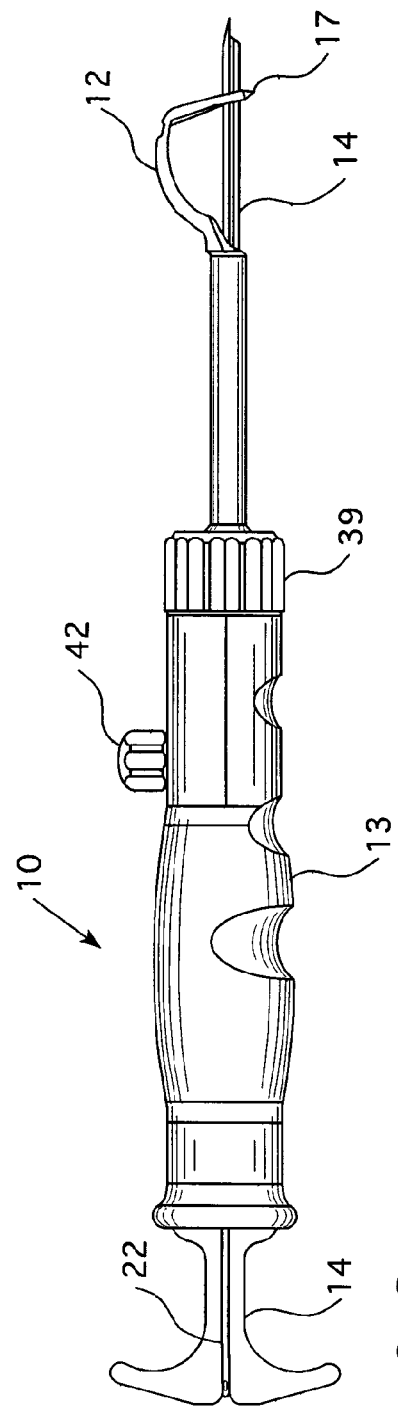
FIG. 2 is a side view of the tunneler shown in FIG. 1 illustrating the suture pushing awl fully inserted and engaged within the tunneler instrument.
Figure 10:
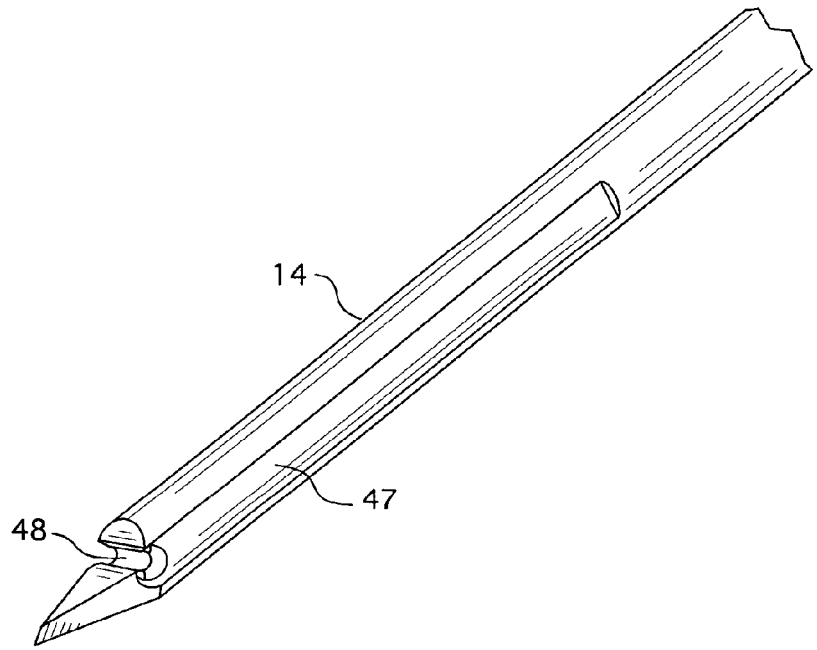
FIG. 10 is an enlarged perspective view of the forward end of the suture pushing awl shown in an inverted position with the suture removed.

Nitinol wires 35 are spaced side by side as best illustrated in FIG. 5 and their bottom free ends are disposed within window 20. Thus when awl pusher 14 is keyed to handle 13 for proper orientation as shown, and is loaded with suture 22 and then penetrated into the bone head 11 to form the lateral tunnel 21 and pushed forward sufficiently to the final position as illustrated in FIG. 2. The distal tip 17 of awl 14 passes between nitinol wires 35 and spreads them and flexes them slightly forward as illustrated in FIG. 10 whereby the nitinol wires 35 tightly engage and capture the suture 22 on both sides of awl 14 to passively capture and retrieve suture 22 from awl 14 when awl 14 is thereafter retracted and withdrawn. The nitinol wires 35 have a bristled surface which captures the suture 22 therebetween under the spring bias of the wires 35.

Nitinol has been selected for the wires 35 as it is a metal alloy of nickel and titanium which exhibits the unique properties of shape, memory and super elasticity. It also may be provided with many different surface finishes. For example, it may be provided with a bristled surface for secure engagement of the suture as by chemical etching or sandblasting, or alternatively may be provided with coated polymers.

Other passive suture capturing and retrieval mechanisms may be substituted for nitinol wires 35, such as a metal trap door, wire mesh, silicone mesh, suture mesh or any other substance that is capable of passively capturing and retrieving the suture 22 from awl 14 such as described hereinafter.

After awl 14 is withdrawn, the captured suture 22 remains clamped between nitinol wires 35 and the distal end of arm 12 may then be withdrawn from medial tunnel 15 pulling the captured suture 22 with it.

Figure 3:
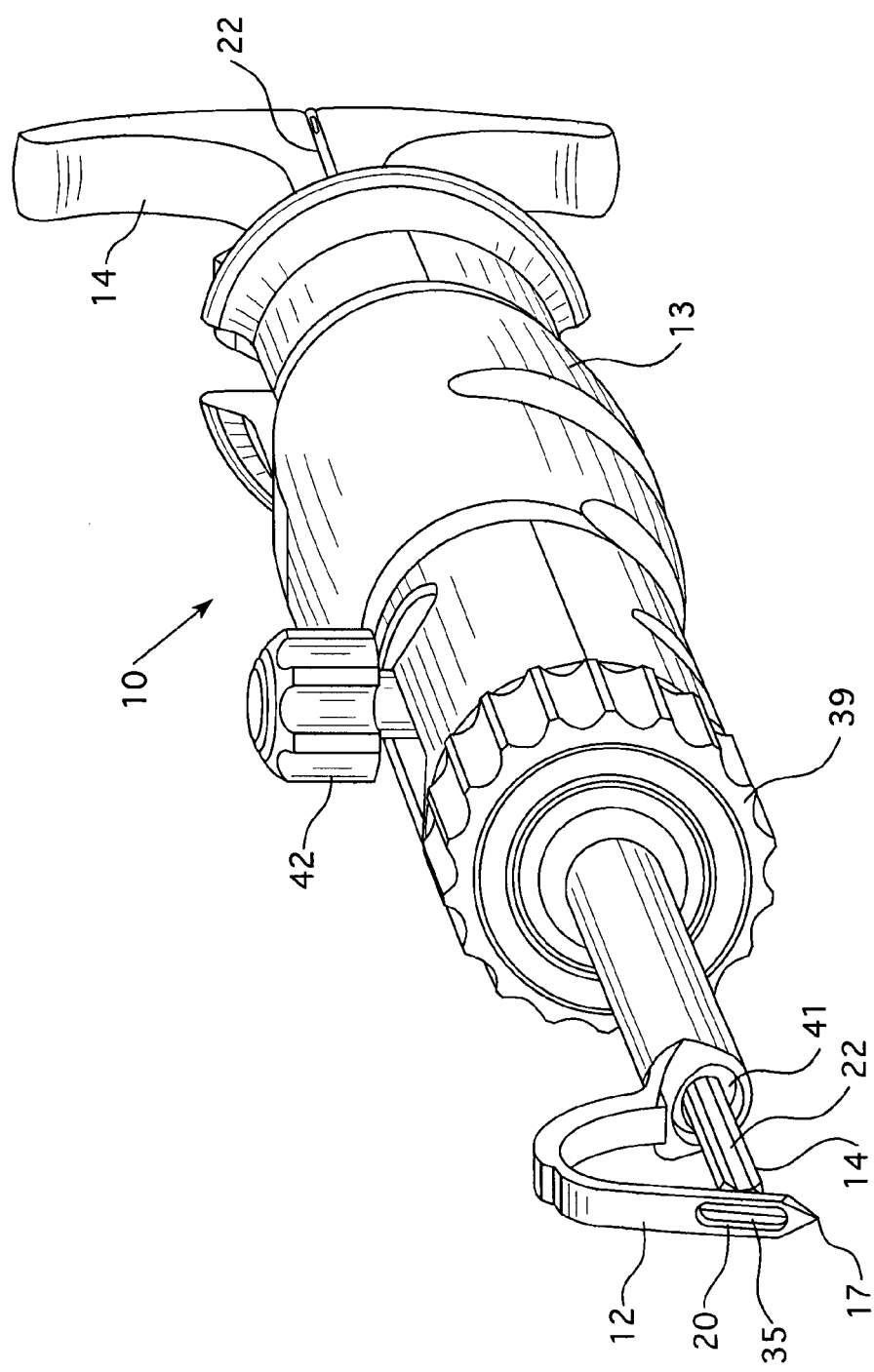
FIG. 3 is a perspective view of the tunneler instrument shown in FIG. 1 as seen from the front.
Figure 6:
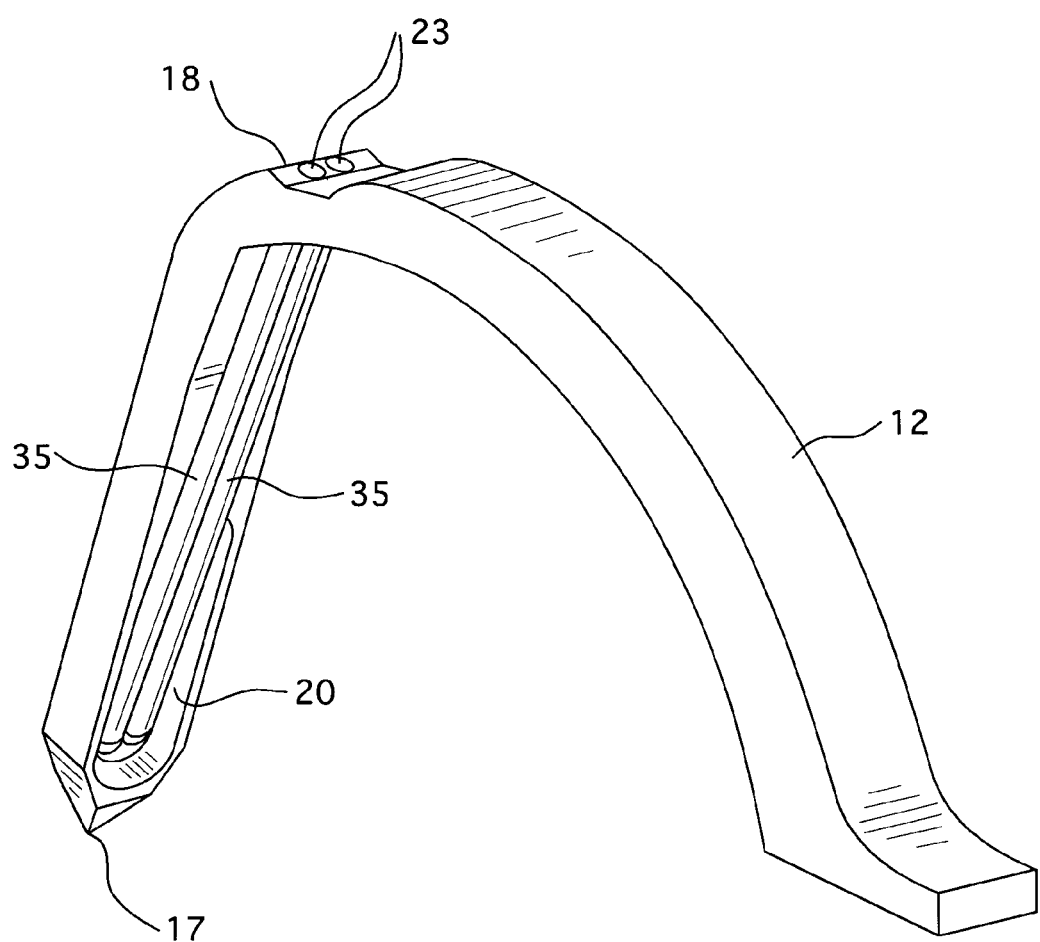
FIG. 6 is a perspective rear view of the passive suture retrieving arm shown in FIG. 4.

Before awl 14 is forced through head 11 to form lateral tunnel 21, inner guide 41 is advanced forward under the bias of spring 31 (FIG. 8) as controlled with knob 42 so that the forward pointed tip 43 of guide 41 (FIGS. 3 and 11) engages the bone of head 11 at the desired position to maintain the instrument 10 in position for advancement of the awl 14.

Figure 7:
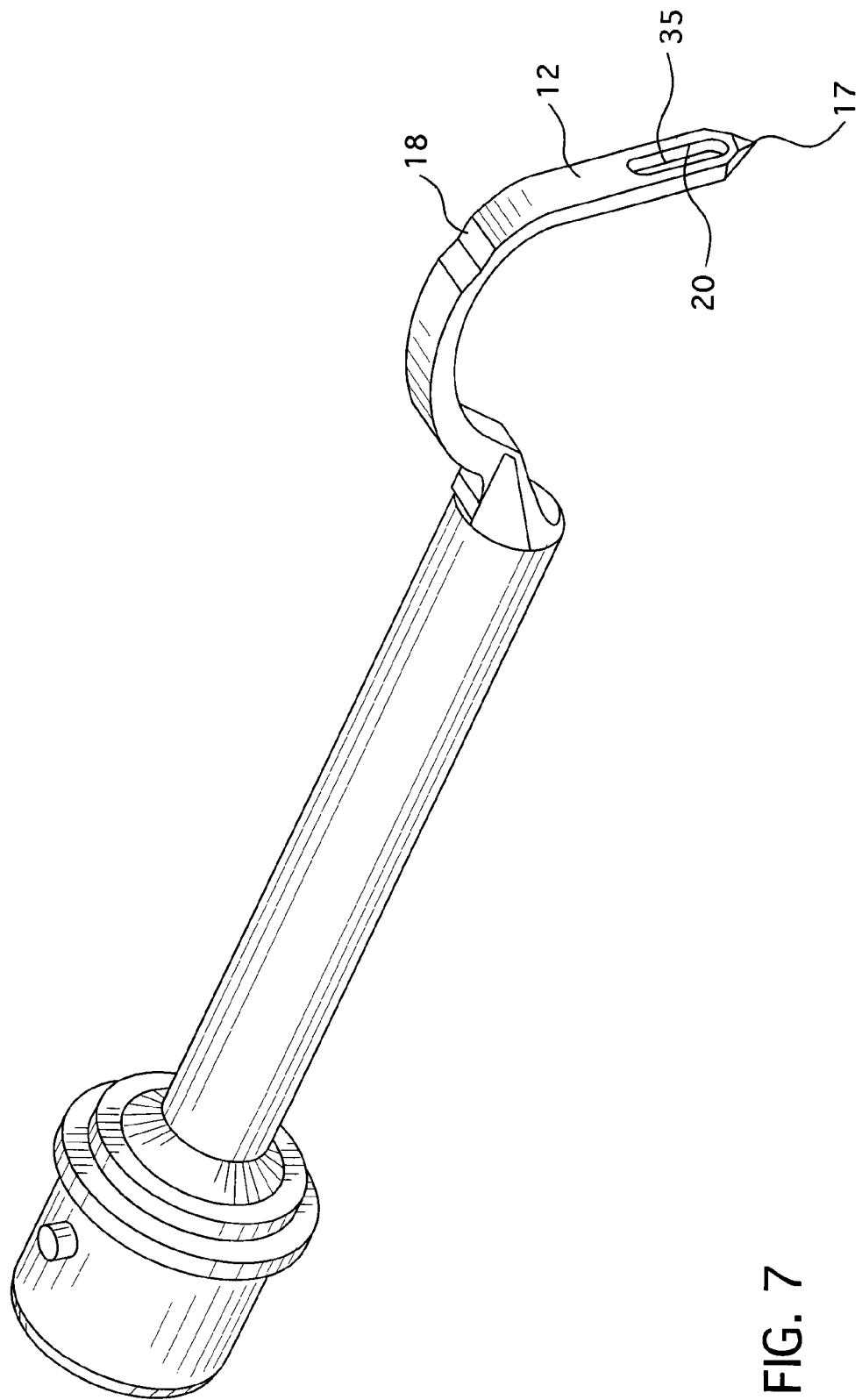
FIG. 7 is an enlarged perspective view of the forward end of the tunneler instrument of the present invention shown as detached from the handle portion of the tunneler instrument of the present invention thereby illustrating in part how the instrument may be disassembled for cleaning and sterilization.
Figure 8:
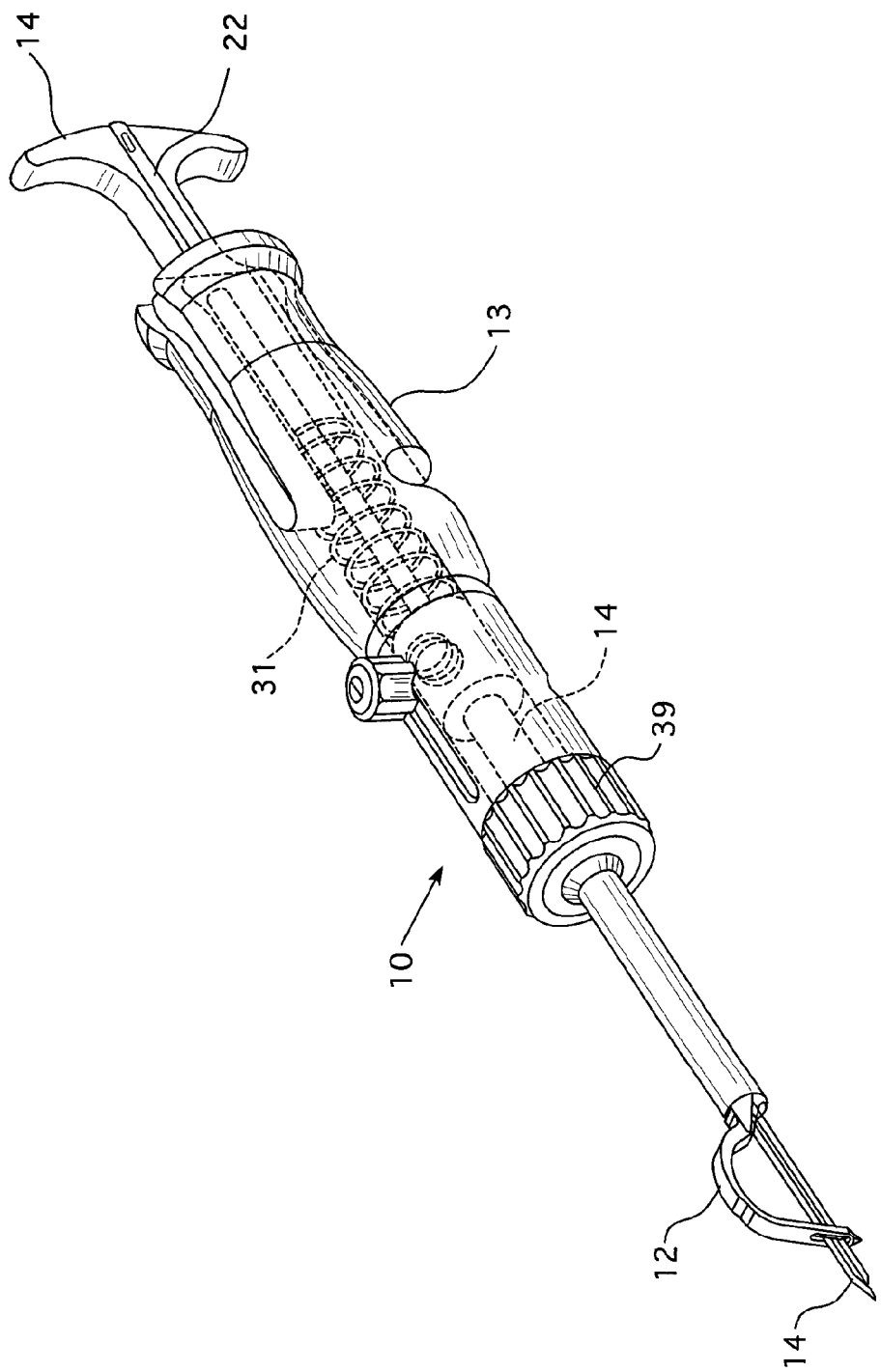
FIG. 8 is a perspective view of the tunneler instrument of the present invention showing and illustrating the internal parts to further illustrate the inner workings of the instrument and its capability to be fully disassembled for cleaning and sterilization.

The tunneler instrument 10 is modular in construction and may be easily disassembled for cleaning and sterilization for reuse. As seen in FIG. 8, the forward collar 39 may be unscrewed in order to detach the forward end of the tunneler 10 as shown in FIG. 7. This also permits removal of the remaining internal parts. Knob 42 may be unscrewed thereby releasing the internal guide 41 and spring 31 for cleaning and sterilization.

Different passive suture retrieval guide arms 12 may be substituted in order to provide guide tips with different morphologies, which guide tips may be interchangeable intraop to allow lower or different positions on the bone, or to adapt to certain intraop situations.

Referring to FIG. 12, the nitinol wires 35 are replaceable for reuse of the instrument. In this embodiment the distal ends 50 are engaged by stainless steel ribbon spring 51 to temporarily but firmly engage and retain nitinol wires 35 in position. Ribbon spring 51 is retained in position by machine screw 52.

Referring next to FIG. 13, a metal trap doors passive suture capture device 35' is illustrated in substitution of the nitinol wires previously described. In this embodiment the trap door 35' consists of two side by side vertical sheets of stainless steel which are respectively retained at the side edges of window 20. The two sheets are separate from each other and meet or adjoin at the middle joint 53.

Accordingly, when the forward tip 17 of awl 14 engages the trap door 35', tip 17 penetrates through and between the two side by side metal plates or sheets, thereby separating them and flexing them forward whereby the inner side edges of the metal sheets at 53 engage awl 14 under a pinching spring biased engagement sufficient to prevent withdrawal of suture 22 from the window 20 when awl 14 is withdrawn from window 20.

Yet another embodiment of the passive suture capture device is illustrated in FIG. 14 is a flexible and percutaneously penetrable wall of one or more layers of a fine mesh 35". In this embodiment, the fine mesh 35" permits penetration of the tip 17 of awl 14 through the mesh causing the fibers of the mesh to spread and engage the awl tip with a tight pinching engagement for assured passive capture of the suture 22 carried on awl 14.

Figure 15:
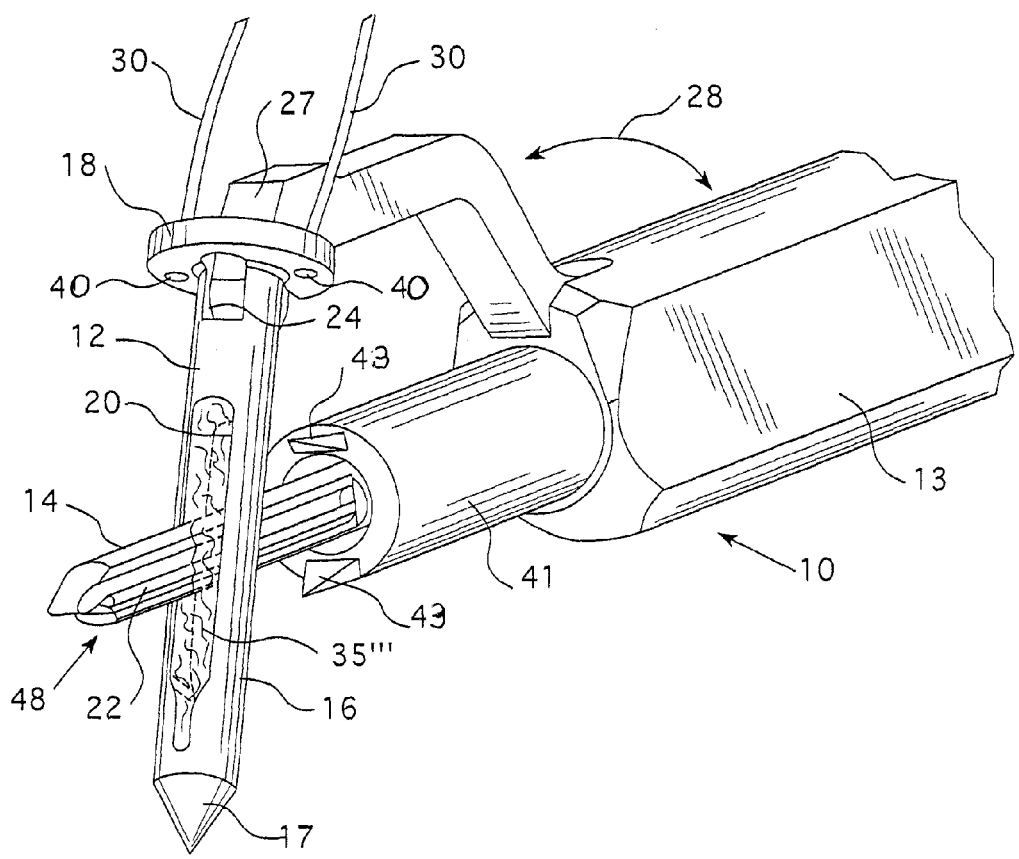
FIG. 15 is an enlarged perspective view of the forward end of the tunneler instrument of the present invention illustrating the suture retrieving arm including a bone tunneling spike attached to its forward end and illustrating yet another embodiment of the passive suture capture device in the form of a wall or sleeve of silicone.

Referring to FIG. 15, the suture retrieving arm 12 in this embodiment consists of two interconnected elements, namely the forward arm 27 which is interconnected with the distal tunneling spike 16 which contains the window 20. In this arrangement, the spike 16 is first driven into the humeral bone to form a first or medial tunnel and then the forward end of arm 27 is secured to the head 18 of spike 16. Thereafter in the afore described fashion, the lateral tunnel is then made with awl 14, which passes through window 20.

In this embodiment the passive suture capture device is provided in the form of a capture wall of silicone 35''' which is flexible and percutaneously penetrable, will engage awl 14 under spring bias thereby pinching the suture 22 against awl 14 sufficiently to prevent withdrawal of the suture 22 from window 20 when awl 14 is withdrawn or retracted.

The head 18 of suture retriever spike 16 is cannulated axially as indicated at 23 and slotted radially at 24 to allow for mounting of the spike 16 into the distal connecting end 25 to temporarily to a driver (not shown) for driving spike 16 into the bone 11.

A long loop 30 of suture or wire is secured via passages 40 to head 18 of spike 16 and permits the surgeon or assistant to pull the spike 16 out of the bone 11 when desired to retrieve suture 22. The end of this loop 30 stays well outside of the body at all times, allowing the surgeon or assistant to readily grab it with their hand and pull.

In the embodiment of FIG. 15, the suture retrieving arm 12 is pivotal as indicated by arrow 28 which allows for vertical pivotal rotation of pitch of the guide handle 13 relative to the spike 16. To the contrary, in the previous embodiments, the suture retrieving arm 12 is fixed relative to the guide handle 13.

We claim:

1. A passive retrieving interosseous suture passing instrument comprising;
   a guide handle having a proximal end for manual grasping and a distal end for engagement with a bone to which suture is to be attached, said bone provided with a first tunnel;
   a suture retrieving arm carried at the distal end of said guide handle and having a distal tip dimensioned to be received in said first tunnel and having a window therethrough which is aligned with a central guide bore passing through said handle for receiving a bone tunneling implement to form a second tunnel in the bone which passes through said window;
   a suture passing awl dimensioned and configured to be received in said central guide bore and carry and pass suture through said window for capture and retention in said window;
   the instrument characterized by a passive suture capture device in said window adapted to passively engage and capture suture carried on said awl under a pinching spring biased engagement sufficient to prevent withdrawal of said suture from said window when said awl is withdrawn;
   said passive suture capture device comprised of a spaced pair of nitinol wires having free distal ends depending into said window and positioned for passage of said awl therebetween under spring biased engagement.

2. The instrument of claim 1, wherein said nitinol wires are replaceable.

3. The instrument of claim 2, including a spring clip on said suture retrieving arm retaining proximal ends of said wires.

4. The instrument of claim 1, wherein said awl is keyed to said handle for guided orientation relative to said handle when fully seated therein and is pointed at its distal end for creating a bone tunnel while simultaneously carrying said suture exposed on sides thereof.

5. The instrument of claim 1, wherein said suture retrieving arm includes a detachable oriented bone tunneling spike at its forward end, said spike carrying said window at its distal end.

* * * * *